United States Patent [19]

Furukawa

[11] 4,334,016
[45] Jun. 8, 1982

[54] HUMAN OSTEOGENIC SARCOMA CELL LINE AND USE THEREOF FOR IMMUNOFLUORESCENT ANTIBODY TEST

[75] Inventor: Toru Furukawa, Philadelphia, Pa.

[73] Assignee: The Wistar Institute of Anatomy and Biology, Philadelphia, Pa.

[21] Appl. No.: 161,005

[22] Filed: Jun. 19, 1980

[51] Int. Cl.$^3$ .......................... C12Q 1/70; C12N 5/02
[52] U.S. Cl. .......................................... 435/5; 435/7; 435/241; 435/948; 23/230 B; 424/8
[58] Field of Search ...................... 435/5, 7, 241, 262, 435/41, 238, 948; 424/8, 12; 23/230 B

[56] References Cited

U.S. PATENT DOCUMENTS 4,229,532 10/1980 Tolbert et al. ...................... 435/948

OTHER PUBLICATIONS

Furukawa, T. et al.; "Demonstration of Immunoglobin G Receptors Induced by Human Cytomegalovirus"; J. Clin. Microb.; vol. 2, No. 4, pp. 332–336 (1975).
Rapp, F. et al.; "The Immunofluorescent Focus Technique in Studying the Replication of Cytomegalovirus"; J. Immunol.; vol. 91, pp. 709–719 (1963).
Schmitz, H. et al.; "Determination of Different Cytomegalovirus Immunoglobulins (IgG,IgA,IgM) by Immunofluorescence"; Arch. geo Virus Forsch; vol. 37, pp. 131–140 (1972).
Furukawa, T. et al.; "Persistent Infection of Human Osteogenic Sarcoma Cells with Human Cytomegalovirus"; Abstracts of the Annual Meeting of ASM, 379, May 1979.
McAllister, R. M. et al.; "Cultivation in Vitro of Cells Derived from a Human Osteosarcoma"; Cancer, vol. 27, pp. 397–402 (1971).
Klement, V. et al.; "Differences in Susceptibility of Human Cells to Mouse Sarcoma Virus"; Nat. Cancer Inst., vol. 47, pp. 65–71 (1971).
Rhem, J. S. et al.; "Non-Producer Human Cells Induced by Murine Sarcoma Virus"; Int. J. Cancer; vol. 15, pp. 23–29 (1975).
Krech V. et al.; Z. Immun. Forsch, vol. 143, pp. 354–362 (1972).
Betts, R. F. et al.; Journal Clinical Microbiology, vol. 4, pp. 151–156 (1976).
Keller, R. et al.; "An IgG–Fe Receptor Induced in Cytomegalovirus–Infected Human Fibroblasts"; J. Immunol., vol. 116, pp. 772–777 (1976).
Westmoreland, D. et al.; J. Immunol., vol. 116, pp. 1566–1570 (1976).
Kettering, J. D. et al.; J. Clinical Microbiol., vol. 6, pp. 627–632 (1977).
McAllister, R. M. et al.; Virology, vol. 19, pp. 521–531 (1960).
Stagno, S. et al.; Jour. Clinical Microbiol., vol. 7, pp. 486–489 (1978).
Rao, N. et al.; Jour. Clinical Microbiol., vol. 6, pp. 633–638 (1977).

Primary Examiner—Benoit Castel
Attorney, Agent, or Firm—Howson and Howson

[57] ABSTRACT

A human osteogenic sarcoma cell line chronically infected with human cytomegalovirus having a substantially constant ratio between immunofluorescent positive and noninfected cells useful in the immunofluorescent serological test for determining the presence of human cytomegalovirus antibody.

1 Claim, 1 Drawing Figure

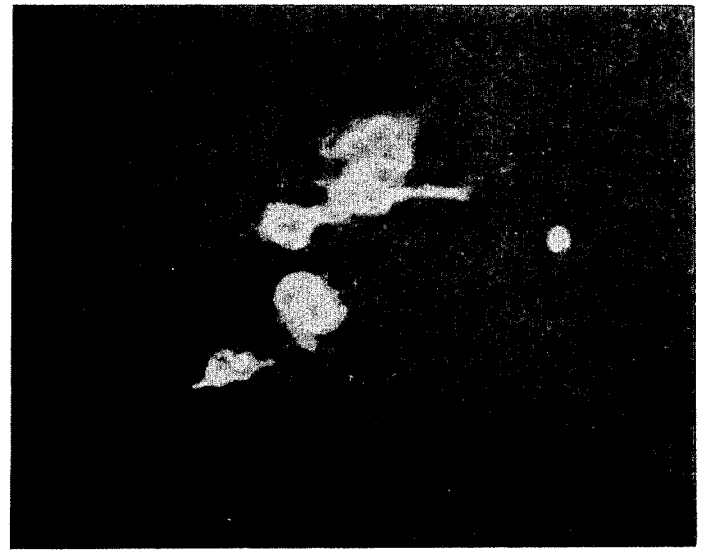

HUMAN OSTEOGENIC SARCOMA CELL LINE AND USE THEREOF FOR IMMUNOFLUORESCENT ANTIBODY TEST

BACKGROUND OF THE INVENTION

Human cytomegalovirus (HCMV) infection in utero is an important cause of central nervous system damage in newborns. Although the virus is widely distributed in the population, about 40% of women enter pregnancy without antibodies and thus are susceptible to infection. About 1% of these women undergo primary infection in utero. Classical cytomegalic inclusion disease is rare; however, a proportion of the infected infants, including those who were symptom free, are subsequently found to be mentally retarded (Lancet Jan. 5, 1974, pp. 1–5).

Preliminary estimates based on surveys of approximately 4,000 newborns from several geographical areas indicate that the virus causes significant damage of the central nervous system leading to mental deficiency in at least 10%, and perhaps as high as 25%, of infected infants. Assuming that about 1% of newborn infants per year excrete HCMV and that about one fourth of those develop mental deficiency, in the United States this means approximately 10,000 brain-damaged children born per year. This is a formidable number, particularly in view of the ability of these children to survive (J. of Infec. Dis. 123, No. 5,555 (May, 1971)).

Many serological tests have been suggested for the determination of HCMV antibody. Of these, the immunofluorescent test is the most rapid, sensitive and convenient. Unfortunately, technical difficulties have been encountered in the preparation of target cells for use in the latter test. These difficulties are based on the fact that human fibroblasts, which heretofore have been used as the target cells, have a limited life span. Thus, it has been necessary to use human fibroblasts freshly infected with HCMV when preparing target cells. Since the infectivity of HCMV inocula is not stable even when preserved at −70° C., it is difficult to obtain a predictable number of infected cells in each preparation.

OBJECT OF THE INVENTION

A primary object of this invention is a novel human osteogenic sarcoma cell line chronically infected with human cytomegalovirus having a substantially constant ratio between immunofluorescent positive and non-infected cells useful in the immunofluorescent serological test for determining the presence of HCMV antibody.

Another primary object of this invention is a novel process for the production of a human osteogenic cell line chronically infected with HCMV.

Still another object of this invention is an improved immunofluorescent test for determining the presence of HCMV antibody in human sera.

These and other objects of this invention will become further apparent from this specification, appended claims and drawing which is a fluorescent micrograph of persistently infected human osteogenic cells by HCMV (200 x) according to this invention.

SUMMARY OF THE INVENTION

A human osteogenic sarcoma cell line chronically infected by HCMV has been produced by infecting human epitheloid cells derived from osteogenic sarcoma in appropriate culture medium with HCMV. After an initial period of three to six, preferably four weeks, during which fresh culture medium is periodically added, e.g. about every five days, the culture is trypsinized, and transferred to new flasks, the split ratio being about 1:4. Thereafter the HCMV infected cells are propagated using standard methods described in the literature each culture being trypsinized and transferred to new flasks at about the aforesaid split ratio every seven days. As taught by the literature (see Exper. Cell Res. 25, 585 (1961) and Virology 16, 147 (1961), the tissue culture system may comprise Eagle's basal medium (BME) or Eagle's minimal essential medium (MEM) in Eagle's balanced salt solution supplemented with prescreened calf serum, the system being buffered at a pH of about 6.8–7.4 with a conventional biological buffering agent such as an alkali metal bicarbonate, carbonate or hydrogen phosphate.

Distinct cytopathic changes do not appear in the cell cultures, but unexpectedly; when examined for HCMV antigen by the immunofluorescent test and infectious center assay on human fibroblasts, a small but relatively constant percentage of the cells, e.g. about 1 to 5 percent are positive in both tests. This substantially constant ratio of infected to uninfected cells is particularly advantageous in that a known number of target cells is available for use in the serological immunofluorescent test for determination of HCMV antibody, which test is discussed in greater detail hereinbelow.

DRAWING

The drawing is a photomicrograph of the cell line E-155 and shows the morphology and intensity of fluorescent stained cells, as well as distinct nuclear inclusion bodies.

DETAILS OF THE INVENTION

The initial cells for producing the novel HCMV infected cell line of this invention may be any human epitheloid cells derived from osteogenic sarcoma, an example of which are the human osteogenic sarcoma clonal cells designated T-85 derived from a 13-year-old caucasian female available from the Cell Culture Laboratory, Navel Biochemical Research Laboratory, Oakland, California, and maintained at The Wistar Institute of Anatomy and Biology, Philadelphia, Pennsylvania.

The human cytomegalovirus may be of any available strain. One such strain is the Towne strain which has a broad antigenic spectrum. This strain was isolated from the urine of a two month old male infant with cytomegalic inclusion disease (symptoms—central nervous system damage and hepatosplenomegaly). This strain of HCMV was isolated by Stanley A. Plotkin, M.D., of The Wistar Institute of Anatomy and Biology and is described in J. Virol. 11 No. 6, 991 (June, 1973).

As indicated above, human osteogenic sarcoma cells in a suitable culture medium are infected with HCMV. The degree of infection is not critical; however, infection at a multiplicity (MOI) of from about 1 to about 100, preferably about 50, is employed, a particularly preferred culture medium being Eagle's minimum essential medium supplemented with 10 percent fetal calf serum.

After the initial incubation period which, as noted, preferably is on the order of about four weeks, the cultures being fed with fresh medium about every fifth day, the cultures are trypsinized and transferred to new flasks at a 1:4 split ratio. The culture medium used initially may be used in the further culture of the cells. After seven days each culture is trypsinized, split 1:4, and the split cultures further propagated as before. In this manner the HCMV infected cell line which is established can be cultivated indefinitely.

The resulting cell line is persistently and chronically infected with HCMV. The cell line which does not have a limited life span grows rapidly and is easily stored in an atmosphere of nitrogen. When reconstituted, the recovery rate of the cell line is excellent. The morphology and the intensity of fluorescent stained cells are clear and show distinct nuclear inclusion bodies. The cell line shows a constant ratio between immunofluorescent positive and non-infected cells.

In order to disclose the nature of the invention still more clearly, the following illustrative examples are given. It is to be understood that the invention is not to be limited to the specific conditions and details set forth in these examples.

EXAMPLE 1

This example describes the preparation of a novel cell line according to this invention.

Subconfluent cultures of human epitheloid clonal cells derived from osteogenic sarcoma clonal cells designated T-85, referred to above, were placed in a plastic flask having a surface area of 75 cm.$^2$ and were infected with the Towne strain of HCMV at MOI 50. Only a small percentage of the cells (about 1 to 10 percent) became infected four days post infection. The infected cells were cultured using Eagle's minimum essential medium (MEM) supplemented with 10 percent fetal calf serum. The cells were fed fresh culture medium every five days.

Four weeks after infection, the cell cultures were trypsinized and transferred to new flasks at a split ratio of 1:4, where the split cell cultures were cultured for seven days using the same culture medium as initially used. The cell cultures were again trypsinized, split 1:4 and again cultured. Using this procedure, the cell line has been cultured for over one year.

The cell line has been designated E-155 by The Wistar Institute of Anatomy and Biology, and has been deposited with said Institute, and with the American Type Culture Collection (ATCC), Rockville, Maryland. Cell Line E-155 has been assigned ATCC No. CRL 8069.

Cell line E-155 has been chronically and persistently infected with HCMV even though distinct cytopathic changes did not appear in the E-155 cultures. When the cultures were examined for HCMV antigen by the immunofluorescence test and infectious center assay on human fibroblasts (see Bishop et al., Plague Assay for Polio Virus and Polio Virus Specific RNAs, page 131, in Fundamental Techniques in Virology (edited by Habel, K., and Salzman, P. N.) Academic Press, 1969), a small percentage of the cells ranging from about 1 to about 5 percent was positive for both tests. The cell line advantageously shows a constant ratio between immunofluorescent positive and non-infected cells (see the FIGURE). Cell line E-155 has an unlimited life span, grows rapidly, is easily stored in nitrogen and exhibits an excellent recovery rate when reconstituted.

As can be seen by reference to the FIGURE, the morphology and the intensity of fluorescent stained cells are clear and show distinct nuclear inclusion bodies.

The specificity for HCMV antibody of cell line E-155 was confirmed using antisera against herpes simplex and varicella Zoster viruses which do not show any fluorescent staining. Antibody titers for HCMV determined on E-155 cells are the same as those on MRC-5 cells, which cells have been described in Nature 227 168 (July 11, 1970), infected with several different HCMV strains, including Towne strain.

By reason of the fact that cell line designated E-155 shows a constant ratio between immunofluorescent positive and non-infected cells, the cell line is particularly useful in carrying out the immunofluorescent serological test.

EXAMPLE II

This example describes the use of the cell line designated E-155 and prepared as set forth in Example I in the immunofluorescent test for determination of the presence of HCMV antibody in a sample of human blood serum.

E-155 cells are trypsinized and seeded $2 \times 10^4$ cells per cm.$^2$ on coverslips, glass slides or chambered slides. 24 to 48 hours after seeding, the cells are washed two times with phosphate-buffered saline solution (pH 7.2) and then fixed with cold acetone at $-10°$ C. for 10 minutes. By this procedure, infected cells are equally distributed in each chamber or on each glass surface.

Blood serum from the blood sample to be tested for presence of HCMV antibody is serially diluted in tenfold dilution with phosphate buffered saline solution (pH 7.2), and the diluted serum is introduced to the seeded slides. After 30 minutes incubation at 37° C., the slide is washed out with saline buffer solution and fluorescein isothiocyanate (FITC) conjugated antihuman immunoglobulin animal serum is introduced to the slide followed by another 30 minute incubation period. The slide is again washed with phosphate buffered saline solution and the slide is viewed under a fluorescent microscope to determine whether immunofluorescent positive cells resulting from reaction between the antigen of the cells and test serum antibodies are present.

What is claimed is:

1. A test procedure for determining the presence of human cytomegalovirus (HCMV) antibody in a sample of human blood which comprises substantially uniformly distributing on a surface as target cells a human osteogenic sarcoma cell line designated ATCC Accession Number CRL 8069 and characterized by an unlimited life span, by being chronically and persistently infected with HCMV, and by showing a substantially constant ratio between cells infected with HCMV and non-infected cells, the percentage of infected cells comprising from about 1 to about 10 percent of the total cells, inoculating said target cells with a diluted sample of blood serum to be tested for the presence of HCMV antibody, contacting the cells with a fluorescein isothiocyanate conjugated immunoglobulin, and optically viewing said cells to determine the presence of immunofluorescent positive cells resulting from reaction between cell antigens and test serum antibodies.

* * * * *